United States Patent [19]

Bartelsen

[11] Patent Number: 4,697,082
[45] Date of Patent: Sep. 29, 1987

[54] PROCESS AND APPARATUS FOR TESTING TRANSPARENT MATERIAL WEBS, PARTICULARLY PLATE GLASS RIBBONS

[75] Inventor: Lutz Bartelsen, Hamminkeln, Fed. Rep. of Germany

[73] Assignee: Flachglas Aktiengesellschaft, Fed. Rep. of Germany

[21] Appl. No.: 807,795

[22] Filed: Dec. 11, 1985

[30] Foreign Application Priority Data

Dec. 14, 1984 [DE] Fed. Rep. of Germany ....... 3445580

[51] Int. Cl.⁴ .............................................. G01N 21/89
[52] U.S. Cl. .................................... 250/341; 250/349; 250/358.1; 250/359.1; 250/360.1; 356/239; 356/431
[58] Field of Search ............ 250/341, 340, 349, 360.1, 250/359.1, 358.1, 572; 356/435, 431, 239

[56] References Cited

U.S. PATENT DOCUMENTS

| | | | |
|---|---|---|---|
| 3,805,073 | 4/1974 | Jayachandra et al. | 250/353 |
| 3,808,439 | 4/1974 | Renius | 250/334 |
| 4,026,656 | 5/1977 | Kusz et al. | 356/51 |
| 4,208,126 | 6/1980 | Cheo et al. | 356/51 |

FOREIGN PATENT DOCUMENTS 3129808 6/1983 Fed. Rep. of Germany .
1338611 11/1973 United Kingdom .

OTHER PUBLICATIONS

Richard Wagner, "Inclusions de Sulfure de Nickel Dans le Verre", Glastechn. Ber., 50 (1977), Nr. 11, S. 296-300.
"Stahl und Eisen", 96 (1976), No. 19, Sep. 23, pp. 913-915.

Primary Examiner—Janice A. Howell
Assistant Examiner—Constantine Hannaher
Attorney, Agent, or Firm—Hill, Van Santen, Steadman & Simpson

[57] ABSTRACT

Process for testing transparent material webs, particularly plate glass ribbons or the like, for material defects, in which the glass ribbon or the like conveyed in its longitudinal direction is scanned over its width in a scanning plane at right angles to its conveying plane and direction by means of a laser-produced flying light spot, the forward and back scattering produced by the inclusions is measured in each case one detection plane sloping with respect to the scanning plane, electrical signals are derived from the measured values obtained and said signals are processed for material defect identification, characterized in that a laser operating in the near IR-range is used as the light spot source, as well as apparatus for preforming this process.

15 Claims, 2 Drawing Figures

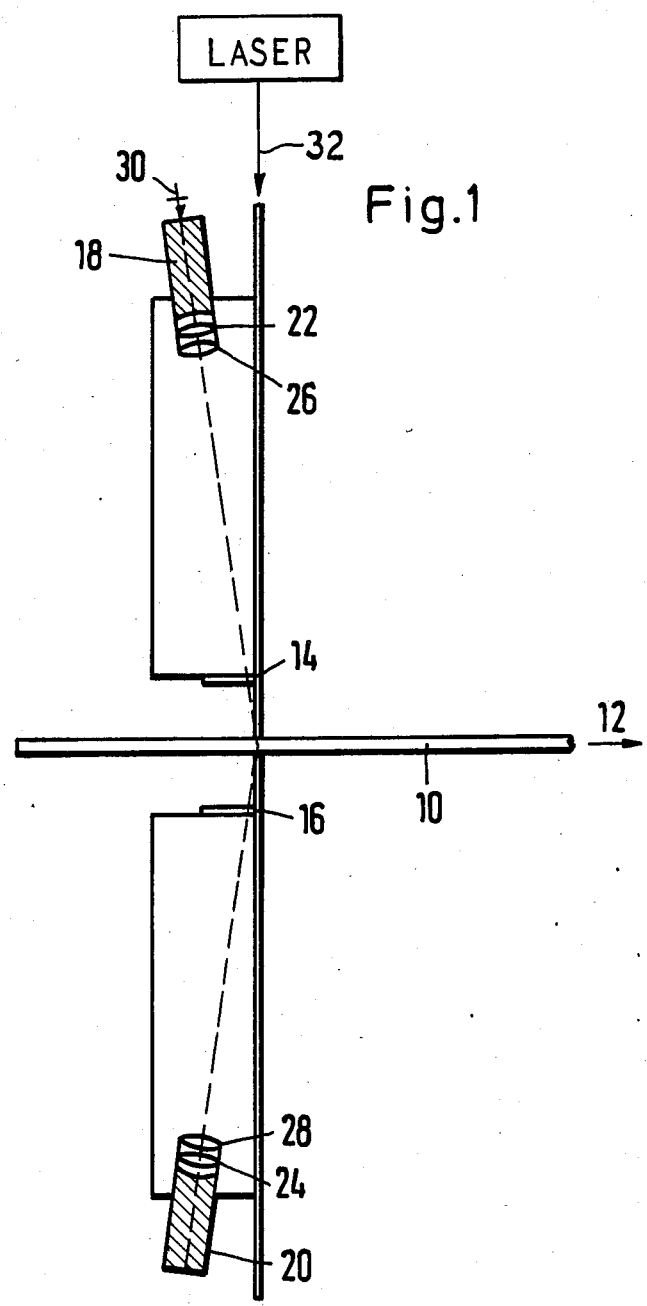

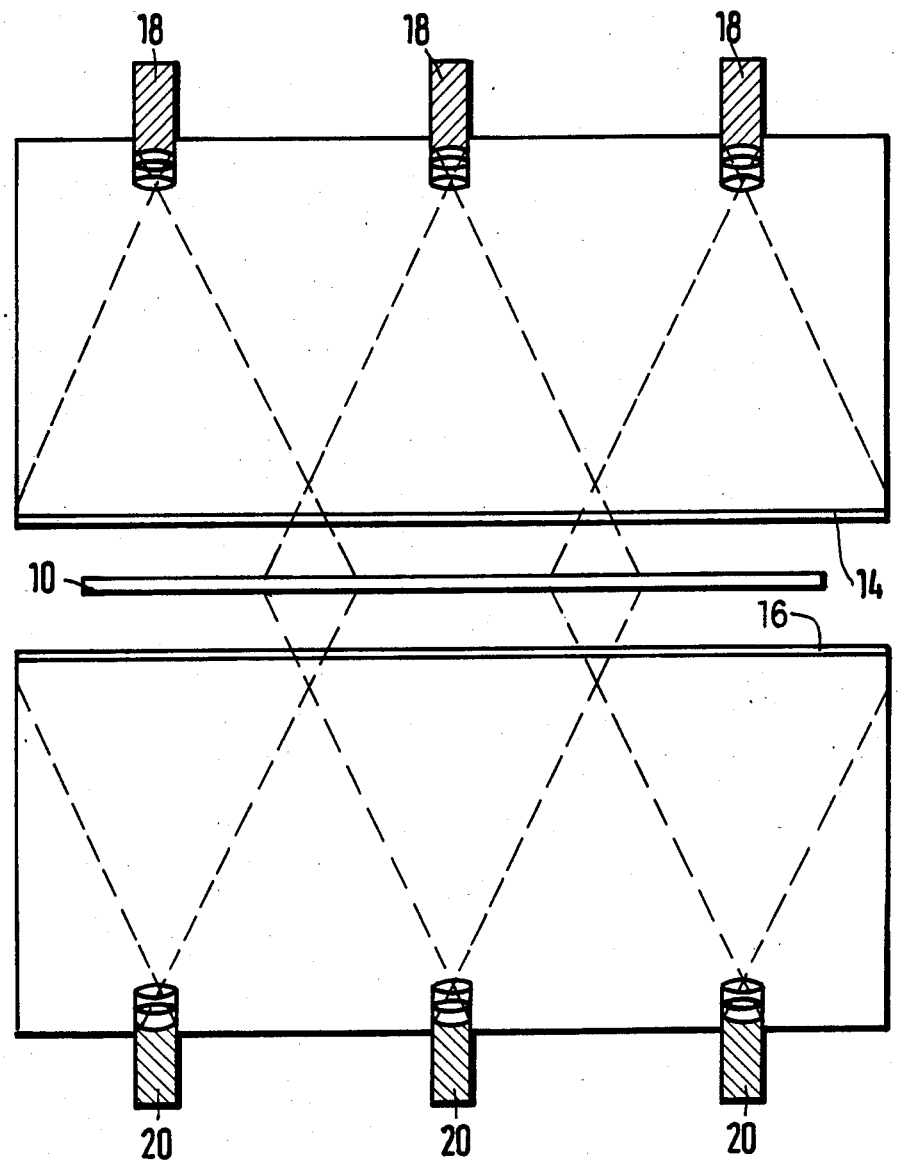

PROCESS AND APPARATUS FOR TESTING TRANSPARENT MATERIAL WEBS, PARTICULARLY PLATE GLASS RIBBONS

BACKGROUND OF THE INVENTION

The present invention relates to a process for testing transparent material webs, particularly flat, plate or sheet glass ribbons or the like for material defects, in which the glass ribbon or the like conveyed in its longitudinal direction is scanned with a laser-produced flying light spot over its width in a scanning plane at right angles to its conveying plane and direction, the forward and back scattering produced by the inclusions is in each case measured in a detection plane sloping with respect to the scanning plane, electrical signals being derived from the measured values obtained and processed for material defect identification. The invention also relates to an apparatus for testing transparent material webs, particularly flat, plate or sheet glass ribbons or the like for material defects, with a light spot source arranged on one side of the glass ribbon or the like conveyed in the longitudinal direction thereof for producing a laser-produced flying light spot scanning the glass ribbon over its width in a scanning plane at right angles to its conveying plane and direction, as well as detectors arranged on either side of the glass ribbon or the like for detecting the forward or back scattering produced by the inclusions in in each case a detection plane sloping with respect to the scanning plane.

In certain circumstances, nickel sulphide (NiS) inclusions in tempered glass plates can lead to spontaneous breakages (Glastechn. Ber, 50 (1977) No. 11, pp 296–300) leading to a not inconsiderable risk to people, particularly in the case of glass facades. In order to avoid the use of such faulty glass plates, it has hitherto been conventional practice to use a so-called heat-soak test, in which following tempering the glass plates undergo an appropriate heat treatment, so that the phase or transition of the NiS-inclusions causing the breakages or shattering is forced beforehand. The glass plates which survive this test without damage can then be used for the glazing of buildings with a much greater shatter-proof protection. However, the aforementioned selection process is unsatisfactory for obvious economic reasons.

British Pat. No. 13 38 611 already discloses a process and an apparatus of the aforementioned type for testing glass ribbons, in which glass ribbons removed e.g. from float glass plants are investigated for material defects. Fundamentally this known process makes it possible to detect NiS-inclusions, in the case of a corresponding highly sensitive setting, but does not make it possible to distinguish these from other glass defects, particularly glass stones. Other similarly functioning glass testing means of this type, such as those known e.g. from German Pat. No. 31 29 808, also permit in the case of a highly sensitive setting, the detection inter alia of NiS-inclusions, without being able to distinguish these from other glass defects and in particular glass stones, so that the aforementioned processes are not suitable for exclusively eliminating glass plates having NiS-inclusions and which are therefore defective, because in this case the said processes would also eliminate those plates having defects not leading to the aforementioned spontaneous breakages, so that an excessive amount of material would be discarded as waste.

Therefore the problem of the invention is to provide a process and an apparatus of the aforementioned type which, compared with the hitherto known processes and apparatuses, permit a better discrimination of the defects found according to type and size and which in particular offer the possibility of distinguishing NiS-inclusions from other glass defects.

SUMMARY OF THE INVENTION

In the case of a process of the aforementioned type, this problem is solved in that a laser operating in the near IR-range is used as the light spot source. A laser with a wavelength of approximately 1060 nm can be used.

The invention also provides for the optional use of a YAG-laser with a wavelength of 1060 nm.

The process according to the invention optionally provides for the angle between the scanning plane and the detection plane to be approximately 5° to 45°. The angle between scanning plane and detection plane can also be approximately 5° to 15°. Optionally, according to the invention, the angle between the scanning plane and the detection plane can be approximately 10°.

The process according to the invention can also be characterized in that a differential signal is formed from forward and back scattering and this is evaluated for material defect discrimination.

The apparatus proposed by the invention, particularly for performing the claimed process, is characterized in that a laser operating in the near IR-range is used as the light spot source.

The light spot source can be a YAG-laser with a wavelength of 1060 nm.

It is also possible to provide a device for forming a differential signal from the forward and back scattering and for the evaluation thereof for defect discrimination.

The angle between the scanning plane (32) and the detection plane (30) can be approximately 5° to 45°. Moreover, the angle between the scanning plane (32) and the detection plane (30) can also be between approximately 5° and 15°. Finally, the apparatus according to the invention can be characterized in that the angle between the scanning plane (32) and the detection plane (30) is approximately 10°.

Due to the fact that, according to the invention, preferably a laser in the near IR-range is used the forward and back scattering is intercepted in angles of approximately 10° or 170°, viewed from the irradiation direction of the light spot and finally the differential signal of the forward and back scattering is electronically evaluated, it is possible to completely satisfactorily discriminate glass defects on the basis of type and size. Such inclusions can be discriminated in a very satisfactory manner due to the clear perference of the back scattering in the case of the scattered radiation caused by the NiS-inclusions under the aforementioned conditions. NiS-inclusions can be satisfactorily distinguished from other standard glass defects in that, according to the invention, use is made of the laser operating in the IR-range, because the reflecting power of NiS rises in the range 0.5 to 2.5μ from approximately 40% to approximately 85%, the use is being recommended of a YAG-laser with a wavelength of 1060 nm (NiS reflecting power approximately 80%), because the wavelength used must be in the high transmission range of the glass and such lasers can be made available without any particular technical problems being involved. At the aforementioned wavelength, the differential signal of the NiS has the reverse sign to the other glass defects, which in particular occur in float glass, so that NiS can be satisfactorily differentiated from other glass defects. The apparatus according to the invention, when performing the inventive process, can clearly distinguish material defects from any conventional glass impurities on the glass surface, such as dust particles and the like, so that the plate glass ribbon or in general the transparent material web does not have to undergo any complicated, costly cleaning before carrying out the testing process.

Further features and advantages of the invention can be gathered from the following description, in which an embodiment is explained relative to the drawings.

BRIEF DESCRIPTION OF THE DRAWINGS

FIG. 1 is a diagrammatic view showing an embodiment of an apparatus according to the invention in section parallel to the conveying direction of the glass ribbon to be tested;

FIG. 2 is a section at right angles to detection plane 30 of FIG. 1.

DESCRIPTION OF THE PREFERRED EMBODIMENT

As can be seen from the drawings, the apparatus used in connection with the represented embodiment is provided, above and below the float glass ribbon 10, which is conveyed in the direction of arrow 12, with in each case one slit 14 or 16 covered by a diffusion screen, the diffusion screens or slits 14, 16 being scanned by means of detectors (photomultipliers) 18, 20, upstream of which are connected filters, 22, 24 and imaging optics 26, 28. The detection plane 30 in which the detectors 18 are arranged slopes at an angle of approximately 10° relative to the scanning plane 32, in which the laser-produced flying light spot is directed onto the glass ribbon 10, the same angle also being set between the detection plane of the detectors 20 arranged below glass ribbon 10 and the scanning plane.

The aforementioned apparatus operates in the following way in connection with the represented embodiment. The glass ribbon 10 to be tested is scanned with a laser beam in the scanning plane at right angles to the ribbon 10 and the glass conveying direction 12. The scanning unit comprises a YAG-laser with a wavelength of 1060 nm and a rotating polygonal mirror. The light scattered by a glass defect encountered by the laser beam is detected by means of the two rows of detectors 18, 20 in the forward and backward directions in detection planes 30 inclined by in each case small angles with respect to the scanning plane and in the represented embodiment by 10°. The detectors are arranged in a parallel line to the scanning line above and below the glass ribbon 10. The differential signal of the forward and backward detectors is evaluated, it being possible to completely satisfactorily distinguish the NiS-inclusions from other glass defects, because the differential signal of NiS at the wavelength used of 1060 nm has the reverse sign to the other glass defects occurring in float glass.

The features of the invention disclosed in the above description, the drawings and claims can be essential for realizing the various embodiments of the invention either singly or in random combinations.

I claim:

1. A process for testing a transparent material web for material defects, comprising the steps of:
   conveying a web in its longitudinal direction;
   scanning a conveyed web with a laser-produced flying spot over its width and at substantially right angles to the conveying plane and direction;
   measuring forward and back scattering produced by the material defects in, in each case, a detection plane sloping with respect to the scanning plane;
   deriving electrical signals from the measured values; and
   processing said signals for material defect identification,
   characterized in that the light spot source comprises a laser operating in the IR-range.

2. A process according to claim 1, characterized in that a laser with a wavelength of approximately 1060 nm is used.

3. A process according to claim 2, characterized in that a YAG-laser with a wavelength of 1060 nm is used.

4. A process according to claim 1, characterized in that the angle between the scanning plane and the detection plane is approximately 5° to 45°.

5. A process according to claim 4, characterized in that the angle between the scanning plane and the detection plane is approximately 5° to 15°.

6. A process according to claim 5, characterized in that the angle between the scanning plane and the detection plane is approximately 10°.

7. A process according to one of the preceding claims, characterized in that a differential signal is formed from the forward and back scattering and is evaluated for material defect discrimination.

8. A process as in claim 1, wherein said web is a glass ribbon and the material defects to be detected are nickel sulphide inclusions.

9. An apparatus for testing a transparent material web for material defects, comprising:
   a laser-produced light source positioned on one side of a web as it is conveyed in its longitudinal direction for producing a flying light spot and said source to scan a conveyed web over its width in a scanning plane at right angles to the conveying plane and direction; and
   detection means arranged on each side of a web for detecting forward and back scattering produced by the material defects in, in each case, a detection plane sloping with respect to the scanning plane,
   characterized in that the light spot source comprises a laser operating in the near IR-range.

10. An apparatus according to claim 9, characterized in that the light spot source is constituted by a YAG-laser with a wavelength of 1060 nm.

11. An apparatus according to claim 9, including means for forming a differential signal from the forward and back scattering and for producing an evaluation thereof for defect discrimination.

12. An apparatus according to claim 9, characterized in that the angle between the scanning plane (32) and the detection plane (30) is approximately 5° to 45°.

13. An apparatus according to claim 12, characterized in that the angle between the scanning plane (32) and the detection plane (30) is approximately 5° to 15°.

14. An apparatus according to claim 13, characterized in that the angle between the scanning plane (32) and the detection plane (30) is approximately 10°.

15. An apparatus as in claim 9, wherein said web is a glass ribbon and the material defects to be detected are nickel sulphide inclusions.

* * * * *